(12) United States Patent
Burgio

(10) Patent No.: US 6,298,265 B1
(45) Date of Patent: Oct. 2, 2001

(54) ELECTRODE DESIGN AND STIMULATOR FOR ANTLER-BEARING ANIMALS

(76) Inventor: Paul A. Burgio, 7377 101 Street North, St. Paul, MN (US) 55110

( * ) Notice: Subject to any disclaimer, the term of this patent is extended or adjusted under 35 U.S.C. 154(b) by 0 days.

(21) Appl. No.: 09/350,831

(22) Filed: Jul. 9, 1999

(51) Int. Cl.[7] .................................................. A61N 1/34
(52) U.S. Cl. ............................................................ 607/2
(58) Field of Search ................................ 607/46, 47, 76, 607/115, 149, 2; 119/812, 813

(56) References Cited

U.S. PATENT DOCUMENTS

| | | |
|---|---|---|
| 4,014,323 | * 3/1977 | Gilmer et al. . |
| 4,781,197 | * 11/1988 | Fukuda . |
| 5,366,489 | 11/1994 | Burgio et al. ........................... 607/47 |
| 5,496,363 | 3/1996 | Burgio et al. ........................ 607/152 |

OTHER PUBLICATIONS

Melzack, R. and P.D. Wall, Pain mechanisms: a new theory, Science 150: 971–979, 1965.

* cited by examiner

Primary Examiner—Scott M. Getzow
(74) Attorney, Agent, or Firm—Knoble & Yoshida, LLC

(57) ABSTRACT

An article for use in applying an electrical stimulus to a pedicle area of an antlered animal includes a clamp for securely attaching the article to the pedicle area and an attached electrode for establishing electrical contact with the pedicle area. The article may be used in conjunction with a transcutaneous electrical nerve stimulation (TENS) system to anesthetize the pedicle area for harvesting purposes, or as part of a system to provide long or short term electrical stimulation to the pedicle in order to enhance blood flow to the area. Processes of applying electrical stimulation to the pedicle area to stimulate growth are also discussed.

10 Claims, 4 Drawing Sheets

ELECTRODE DESIGN AND STIMULATOR FOR ANTLER-BEARING ANIMALS

BACKGROUND OF THE INVENTION

1. Field of the Invention

This invention relates to the field of raising and harvesting antler-bearing animals, such as deer and elk.

2. Description of the Related Technology

Antlered animals such as deer and elk are raised on farms in the United States and other countries to harvest the growing antlers. The growing antler, also called the velvet antler, is sold as a food supplement around the world, particularly in Asia.

Pain control during harvesting or cutting of the antler is of concern since the velvet antler has an abundant nerve supply. The two primary nerves innervating the pedicle are the infratrochlear and zygomaticotemporal branches of the ophthalmic division of the trigeminal nerve. Sensory branches of the first cervical nerves innervate the posterior aspect of the pedicle, as is shown schematically in FIG. 1.

Traditional methods of pain control include injections of local anesthetics and electroimmobilization. The local anesthetics used are those commonly used in human and veterinary medicine. A few to several injections are made around the pedicle (the base of the antler) and near the nerves supplying the antler. The local anesthetic provides a nerve block, which prevents the pain information from reaching the brain. The shortcoming of this procedure is that a number of subcuticular injections have to be made in the proximity of the nerves around the pedicle and then a wait of five minutes must be made for the local anesthetic to take full effect. The injections must be given at the base of the large antlers in a technique that is known as a ring block. Precise injections are difficult, however, since the deer and elk are large and frequently move their heads.

A second traditional method, electroimmobilization, involves placing a first electrode on the nose and a second on the tail or in the anus. The electrical stimulation causes all the animal's muscles to contract, thus immobilizing the animal. The shortcomings of this procedure relate to the stress induced in the animal by immobilizing all body muscles, including those related to breathing. Studies show that the animals appear to experience more stress related to the electroimmobilization than to the cutting of the antlers. Also, the level of stimulation is difficult to adjust so that the animal is immobilized but still the animal can breathe. This method is not used on people so there are no studies on people to determine if this method provides pain control.

A new method of controlling pain during the harvesting of antlers is the use of transcutaneous electrical nerve stimulation (TENS). This technique has been used in people to control pain associated with medical and dental treatments as well as with muscles and joints. The mechanism of action of TENS is most likely based on the blocking of pain at the first nucleus or first neural relay junction. This mechanism is based on the experimental finding of Melzack, R. and Wall, P. D., Pain Mechanisms: a new theory, *Science*, 150: 971–979 (1965). By this mechanism, the electrical stimulation of the sensory nerve fibers works to block pain and prevent the nerve impulses representing pain from reaching the brain. The pain control is most effective when the electrical stimulation is delivered to the area of the pain; this is true for TENS as well as local anesthetics.

When TENS is used today spring clamps are placed at various points on the head. One electrode can be placed on the animal's lip and the other on the ear. Alternatively, one electrode can be placed anterior and the other electrode posterior to the pedicle. Another electrode placement puts one clip on each ear. Then the stimulation is increased slowly over a one to three-minute period until muscle contractions cause the ear to lay down against the neck and/or the eye closes. The antler is then surgically cut and removed. For maximum pain control, the electrodes are repositioned and the unit level of stimulation is increased over one to three minutes before cutting the other antler.

While TENS has proved a viable and effective mechanism for anesthetizing the animals during antler harvesting, the process of attaching and disconnecting the various electrodes is difficult. A need exists for an improved TENS system for applying electrical stimulation to antlered animals that is more effective and more convenient to use than the systems that are presently in use.

SUMMARY OF THE INVENTION

Accordingly, it is an object of the invention to provide an improved TENS system for applying electrical stimulation to antlered animals that is more convenient to use than the systems that are presently in use.

In order to achieve the foregoing and other objects of the invention, an article according to a first aspect of the invention for use in applying an electrical stimulus to the pedicle area of an antlered animal includes a clamping structure for securely attaching the article to a pedicle area of an antlered animal, the clamping structure further being for at least partially for occluding blood flow in the pedicle area; and electrode structure, attached to the clamping structure, for establishing electrical contact with the pedicle area when the clamping structure is attached to the pedicle area.

According to a second aspect of the invention, a system for anesthetizing a pedicle area of an antlered animal includes generator structure for generating an electrical current that is suitable for transcutaneous electrical nerve stimulation (TENS) of a pedicle area of an antlered animal; clamping structure for securely attaching to a pedicle area of an antlered animal; and electrode structure, attached to the clamping structure and in communication with the generator structure, for establishing electrical contact with the pedicle area when the clamping structure is attached to he pedicle area.

According to a third aspect of the invention, a system for stimulating the growth and quality of an antler on an antlered animal includes generator structure for generating an electrical current that is suitable for promoting increased flow of blood within a pedicle area of an antlered animal; clamping structure for securely attaching to a pedicle area of an antlered animal; and electrode structure, attached to the clamping structure and in communication with the generator structure, for establishing electrical contact with the pedicle area when the clamping structure is attached to the pedicle area.

According to a fourth aspect of the invention, a process of anesthetizing a pedicle area of an antlered animal through the use of transcutaneous electrical nerve stimulation (TENS) includes steps of (a) clamping an article that has at least one electrode mounted thereon to the pedicle area in such a manner as to additionally restrict blood flow through the pedicle area; and (b) applying a transcutaneous electrical nerve stimulation current to the pedicle area via the electrode.

According to a fifth aspect of the invention, a process of stimulating blood flow through a pedicle area of an antlered animal includes steps of (a) securing an article that has at least one electrode mounted thereon to a pedicle area of an antlered animal such that the electrode is placed into electrical contact with the pedicle area; and (b) applying a electrical stimulation current to the pedicle area via the electrode.

These and various other advantages and features of novelty that characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

DETAILED DESCRIPTION OF THE PREFERRED EMBODIMENT(S)

Figure 1:
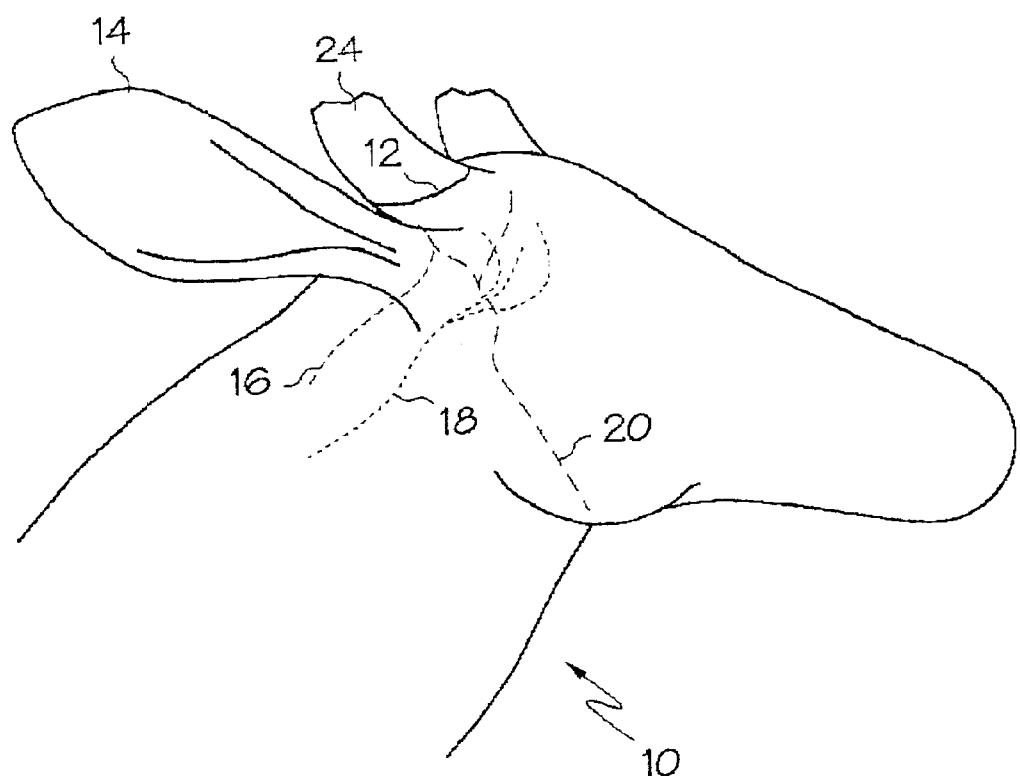
FIG. 1 is a diagrammatical depiction of the anatomy of an antlered animal in the area of the pedicles and antlers.

Referring now to the drawings, wherein like reference numerals designate corresponding structure throughout the views, and referring in particular to FIG. 1, an antlered animal 10 is such as a deer or an elk includes a pair of pedicles 12, which are generally positioned between the ears 14 of the animal. The two primary nerves innervating the pedicles 12 are the infratrochlear branch 16 and the zygomaticotemporal branch 18 of the ophthalmic division of the trigeminal nerve. Sensory branches of the first cervical nerves innervate the posterior aspect of the pedicle, as is shown in FIG. 1. Circulation to the pedicles is provided by the superficial temporal arteries and veins 20, which are also shown in FIG. 1.

The antlers 24 of the animal grow outwardly from the pedicles 12. For purposes of this document, the pedicle area is defined as including the pedicles 12 and the antlers 24.

Figure 2:
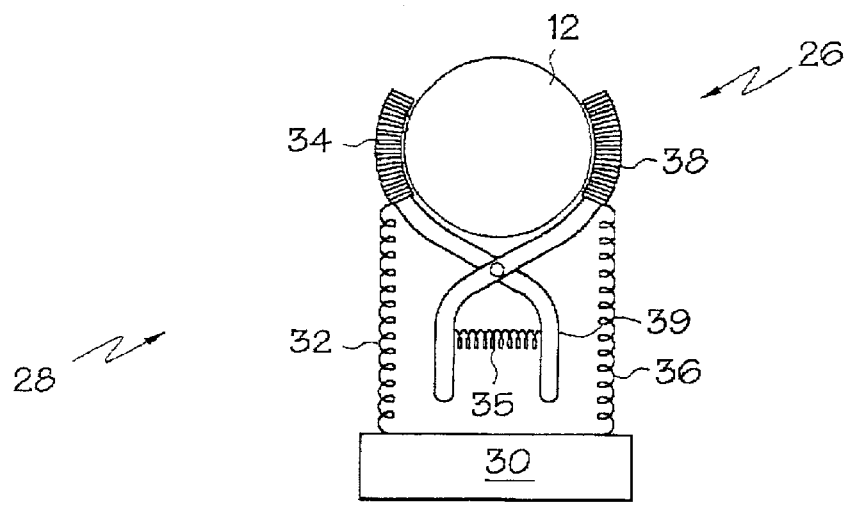
FIG. 2 is a schematic view of a system for applying transcutaneous electrical nerve stimulation (TENS) to a pedicle area of an antlered animal that is constructed according to a first embodiment of the invention.

Referring now to FIG. 2, a system 28 for applying electrical stimulation to a pedicle area of an antlered animal includes a novel and advantageous clamping article 26 that is constructed and arranged to securely attach to a pedicle area of an antlered animal, as well as a generator 30 for generating an electrical current. Preferably, generator 30 is of the type that is suitable for transcutaneous electrical nerve stimulation (TENS) of a pedicle area of an antlered animal. A TENS current is characterized as being a charge-balanced alternating (AC) current and can have different waveforms depending on the effect that is desired. The charge balanced nature of the electrical stimulation results in negligible injection of ions and consequent skin irritation. Also, alternating current (AC) has a different effect on the soft tissue and bone then does direct current (DC). Positive and negative components of the wave can be identical, or one component can have a higher peak and shorter duration than the other component.

As shown schematically in FIG. 2, the clamping article 26 includes a first electrode 34 that is electrically connected to the generator 30 by means of a first wire 32, and a second electrode 38 that is connected to generator 30 by means of a second wire 36. The electrodes 34, 38 are preferably curved so as to be generally complementary in shape to the outer shape of the pedicle area of the animal, and are preferably fabricated, at least on the inner sides thereof, of a conductive material, such as aluminum or copper. The conductive material is electrically connected to the respective wires 32, 36 by means of a standard technique, such as brazing. As may be further seen in FIG. 2, the electrodes 34, 38 are oriented so as to be substantially opposed from each other, and are spring biased together by means of a compressive spring 35, so that they will remain clamped to the pedicle area of the animal. The electrodes 34, 38 may be unclamped from the pedicle area by the user, who will grip a pair of opposed handles 39 on the article 26 that are mounted pivotally to each other so as to act against the biasing of the spring 35 and spread the electrodes 34, 38 apart. Preferably, the article 26 is clamped onto the pedicle area so that the electrodes 34 and 38 press onto the superficial temporal artery and vein 20, thus at least partially occluding blood flow to the pedicle area.

Figure 3:
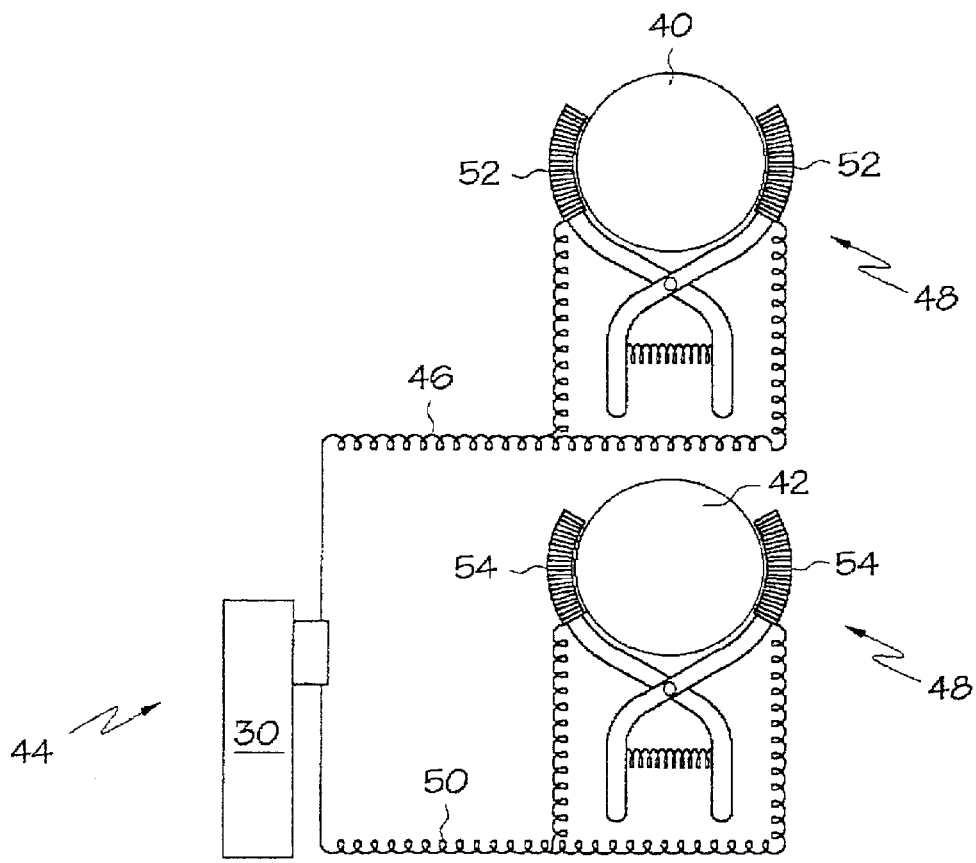
FIG. 3 is a schematic view of a system for applying transcutaneous electrical nerve stimulation (TENS) to a pedicle area of an antlered animal that is constructed according to a second embodiment of the invention.

In a second embodiment of the invention, which is depicted in FIG. 3, a first clamping system 48 is provided for applying electrical stimulation to a first pedicle 40 of an animal, and a second clamping system 48 is provided for applying electrical stimulation to a second pedicle 42 of the same animal. In this embodiment, the first clamping system includes a pair of opposed electrodes 52, both of which are in electrical contact with a generator 30 by means of a single wire 46. The second clamping system similarly includes a pair of opposed electrodes 54, which are likewise in contact with the generator 30 by means of a second wire 50. A switch 44 is provided on the generator 30 to change the polarity of the electrical current is being applied. Studies in humans have demonstrated that the positive lead is more active and provides more effective pain control in this area of the electrode when using a charge-balanced square wave, a common waveform used in TENS stimulators. Switch 44 would allow the polarity to be changed on the lead on the opposite antler to provide more effective pain control just before removing the opposite antler. The stimulation would not have to be turned off, thus saving time for the operator, and reducing stress on the animal.

Figure 4:
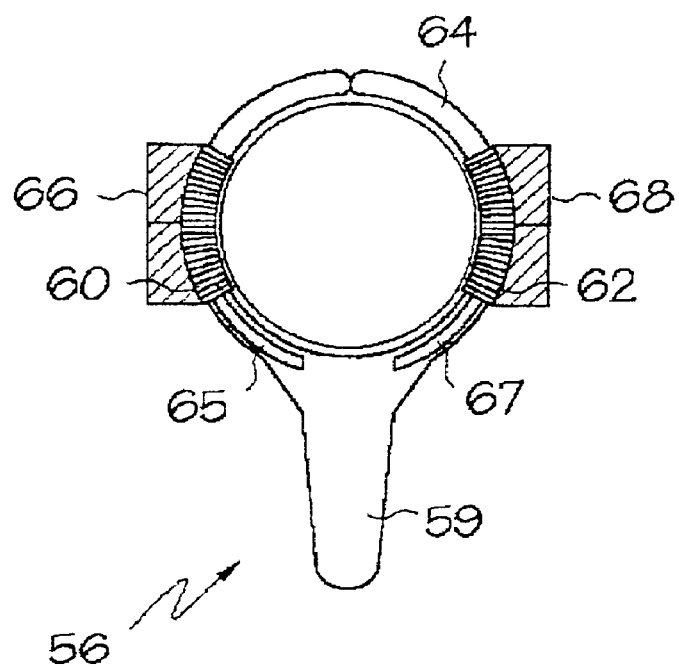
FIG. 4 is a clamping unit that is constructed according to a preferred embodiment of the invention.

FIG. 4 illustrates a clamping article 56 that is constructed according to an alternative embodiment of the invention. In this embodiment, clamping article 56 includes a handle 58 that is grippable by an operator and includes a first open channel 60 on one side thereof, and a second open channel 62 at an opposite side thereof. Clamping article 56 further includes the band 64 of latex tubing or other elastomeric material that has a first knot 65 made in one end thereof and a second knot 67 in an opposite end thereof. A first electrode is secured to one portion of the tubing 64 and a second electrode member is secured to another portion of the latex tubing 64 and is spaced from the first electrode so that the second electrode will be substantially opposed in position from the first electrode 66 when it is clamped on to the pedicle area of the animal. In operation, an operator will first secure the first knot 65 within the open channel 60 of the handle 58, then will wrap the latex tubing 64 about the pedicle area of the animal, drawing it tight, and then securing the second knot 67 of the tubing 64 in the second open channel 62, thus completing the clamping of the tubing 64 about the pedicle area. The tubing 64 will thus hold the electrodes 66 tightly against the pedicle area, and will further act as a tourniquet, thereby at least partially occluding blood flow in the pedicle area.

Figure 5:
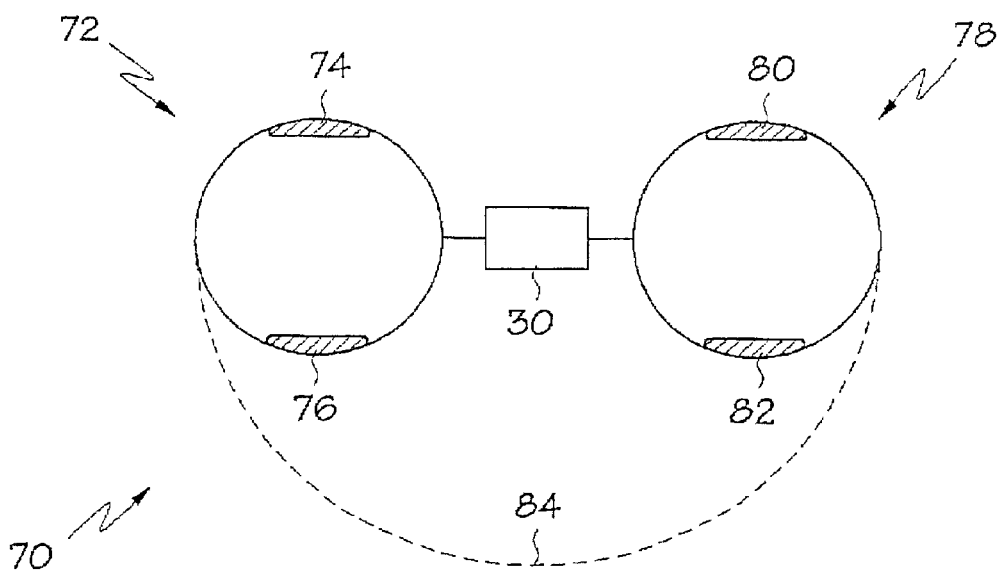
FIG. 5 is a system according to one embodiment of the invention for applying electrical stimulation to a pedicle area of an antlered animal for the purpose of enhancing blood flow.
Figure 6:
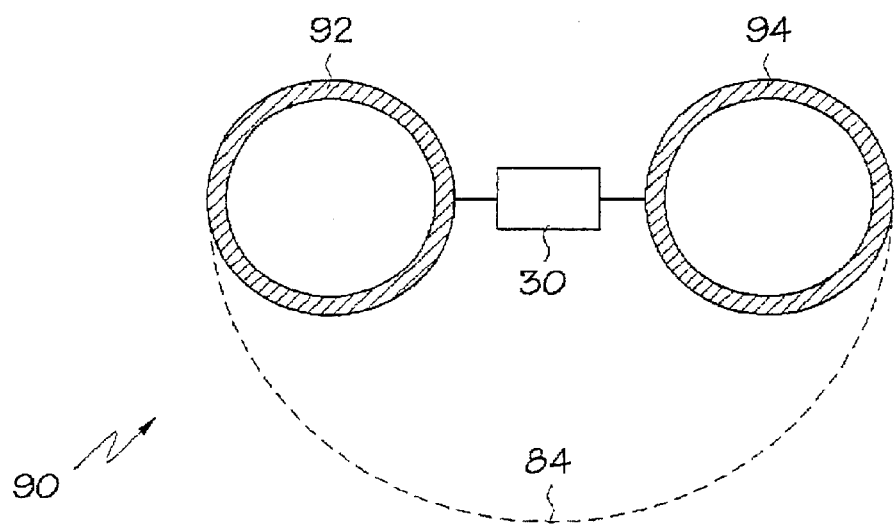
FIG. 6 is a system according to a second embodiment of the invention for applying electrical stimulation to a pedicle area of an antlered animal for the purpose of enhancing blood flow.

Referring now to FIGS. 5 and 6, another advantageous aspect of the invention involves the use of a TENS generator 30 or other electrical stimulation apparatus to stimulate growth and delay calcification in the pedicle area. Looking first to FIG. 5, a system 70 for applying electrical stimulation to the pedicle area of an animal for this purpose includes a first electrode assembly 72 having an electrode 74 of a first polarity and an opposing electrode 76 of a second polarity. System 70 further includes a second electrode assembly 78 having a first electrode 80 of a first polarity and an opposing electrode 82 of a second polarity. The electrodes 74, 80 that are of the first polarity are appropriately connected to a generator unit 30, as are the electrodes 76, 82 that are of the second polarity. According to one particularly advantageous aspect of the invention, the generator unit 30 is constructed so as to be lightweight and portable and to have a self-contained power source, and is secured to the animal by means of an elastic band 84 or other harness so that the animal can roam freely without constraint as electrical stimulation is being applied.

In the embodiment of FIG. 6, a first electrode 92 is secured about one pedicle area of the animal, and a second electrode 94 is secured to the other pedicle area of the same animal. The first electrode 92 is connected to a first polarity of the generator 30, while the second electrode 94 is connected to a second polarity of the generator 30. Preferably, generator 30 includes a switch for reversing polarity as has previously been described with reference to the embodiment of FIG. 3. As in the embodiment of FIG. 5, the system 90 is secured to the animal by means of an elastic band 84 or other appropriate harness.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A process of anesthetizing a pedicle area of an antlered animal through the use of transcutaneous electrical nerve stimulation (TENS), comprising steps of:
   (a) clamping an article that has at least one electrode mounted thereon to the pedicle area in such a manner as to additionally restrict blood flow through the pedicle area; and
   (b) applying a transcutaneous electrical nerve stimulation current to the pedicle area via the electrode.

2. A process according to claim 1, wherein step (b) comprises applying an alternating current (AC) type nerve stimulation current to the pedicle area via the electrode.

3. A process according to claim 1, wherein step (a) is performed by clamping the article so as to occlude blood flow through the superficial temporal artery.

4. A process according to claim 1, wherein step (a) is performed with a first electrode that is positioned to establish electrical contact with a first portion of the pedicle area, and a second electrode that is positioned to establish electrical contact with a second portion of the pedicle area.

5. A process according to claim 1, further comprising a step of securing a second article that has at least a second electrode mounted thereon to a second pedicle area of an antlered animal, and wherein step (b) is performed by applying a TENS current between the first and second electrodes.

6. A process of stimulating blood flow through a pedicle area of an antlered animal comprising steps of:
   (a) securing an article that has at least one electrode mounted thereon to a pedicle area of an antlered animal such that the electrode is placed into electrical contact with the pedicle area; and
   (b) applying a electrical stimulation current to the pedicle area via the electrode.

7. A process according to claim 6, wherein step (b) comprises applying an alternating current (AC) type nerve stimulation current to the pedicle area via the electrode.

8. A process according to claim 1, wherein step (a) is performed with a first electrode that is positioned to establish electrical contact with a first portion of the pedicle area, and a second electrode that is positioned to establish electrical contact with a second portion of the pedicle area.

9. A process according to claim 1, further comprising a step of securing a second article that has at least a second electrode mounted thereon to a second pedicle area of an antlered animal, and wherein step (b) is performed by applying a stimulation current between the first and second electrodes.

10. A process according to claim 1, further comprising a step of securing the article to an antlered animal with a power source that is carried by the animal, whereby the animal can move without constraint.

* * * * *